(12) United States Patent
Dirks (10) Patent No.: US 11,898,945 B2
(45) Date of Patent: Feb. 13, 2024

(54) MICROTOME BLADE GUARD WITH INTEGRATED BLADE ALIGNMENT DEVICE

(71) Applicant: Sakura Finetek U.S.A., Inc., Torrance, CA (US)

(72) Inventor: Lawrence H. Dirks, San Pedro, CA (US)

(73) Assignee: SAKURA FINETEK U.S.A., INC., Torrance, CA (US)

(*) Notice: Subject to any disclaimer, the term of this patent is extended or adjusted under 35 U.S.C. 154(b) by 27 days.

(21) Appl. No.: 17/025,937

(22) Filed: Sep. 18, 2020

(65) Prior Publication Data

US 2022/0090990 A1   Mar. 24, 2022

(51) Int. Cl.
  *G01N 1/06* (2006.01)
  *B26D 5/08* (2006.01)
  *A61B 10/02* (2006.01)

(52) U.S. Cl.
  CPC .......... *G01N 1/06* (2013.01); *A61B 10/0266* (2013.01); *B26D 5/086* (2013.01); *G01N 2001/061* (2013.01); *G01N 2001/065* (2013.01)

(58) Field of Classification Search
  CPC ............... G01N 1/06; G01N 2001/061; G01N 2001/065; A61B 10/0266; B26D 5/086
  See application file for complete search history.

(56) References Cited

U.S. PATENT DOCUMENTS

| | | | |
|---|---|---|---|
| 3,699,830 A | 10/1972 | Pickett | |
| 4,472,989 A * | 9/1984 | Endo | G01N 1/06 83/699.61 |
| 4,700,600 A * | 10/1987 | Pickett | G01N 1/06 83/915.5 |
| 5,099,735 A * | 3/1992 | Kempe | B26D 7/2614 83/699.61 |
| 5,669,278 A | 9/1997 | Metzner | |

(Continued)

FOREIGN PATENT DOCUMENTS

| CN | 105865833 A | 8/2016 |
|---|---|---|
| CN | 106239608 B | 7/2018 |

(Continued)

OTHER PUBLICATIONS

Related Application, Australian Patent Application No. 2021225207, Sakura Finetek U.S.A., Inc., Examiner's First Report; dated Sep. 15, 2022.

(Continued)

*Primary Examiner* — Jonathan G Riley
(74) *Attorney, Agent, or Firm* — William Thomas Babbitt (57) ABSTRACT

A microtome blade guard including a first arm operable to be coupled to a first side of a cutting mechanism of a microtome; a second arm operable to be coupled to a second side of a cutting mechanism; a lateral support member disposed between the first arm and the second arm; and a staff coupled to the lateral support member and operable to extend therefrom to engage a blade positioned in the blade slot. A microtome including a blade guard and a method including placing a blade in a blade slot of a blade block of a microtome; engaging the blade with a staff coupled to a blade guard that is coupled to the blade block; and moving the blade with the staff.

16 Claims, 9 Drawing Sheets

(56) References Cited

U.S. PATENT DOCUMENTS

| | | | | |
|---|---|---|---|---|
| 5,851,213 | A | * | 12/1998 | Berleth .................... G01N 1/06 83/167 |
| 8,042,444 | B2 | | 10/2011 | Thiem |
| 9,304,064 | B2 | | 4/2016 | Walter |
| 2004/0194604 | A1 | | 10/2004 | Fischer |
| 2009/0235799 | A1 | * | 9/2009 | Thiem .................. B26D 7/2614 83/651 |
| 2011/0030523 | A1 | | 2/2011 | Fank |
| 2014/0033888 | A1 | * | 2/2014 | Walter .................... G01N 1/06 83/698.11 |
| 2018/0136087 | A1 | | 5/2018 | Bui et al. |

FOREIGN PATENT DOCUMENTS

| | | |
|---|---|---|
| CN | 209111189 U | 7/2019 |
| CN | 210389447 U | 4/2020 |
| CN | 109291128 B | 10/2020 |
| DE | 102012213824 A1 | 2/2014 |
| DE | 102019130995 A1 | 5/2021 |
| JP | 3033094 U | 10/1996 |
| JP | 2002517715 A | 6/2002 |
| JP | 2008518217 A1 | 9/2009 |
| JP | 2012037309 A | 2/2012 |
| WO | 2006045270 A1 | 5/2006 |
| WO | 2022/051978 A1 | 3/2022 |

OTHER PUBLICATIONS

Related Application, Canadian Patent Application No. 3,130,960, Sakura Finetek U.S.A., Inc., Examiner's Report; dated Dec. 19, 2022.

Related Application, Japanese Patent Application No. 2021-144466, Sakura Finetek U.S.A., Inc., Notice of Rejection; dated Sep. 21, 2022.

Sakura Fintenek U.S.A., Inc., Related Application, Canadian Patent Application No. 3,130,960, Requisition by The Examiner in Accordance With Subsection 86(2) of the Patent Rules, dated May 27, 2022.

Sakura Fintenek U.S.A., Inc., Related Application, International European Patent Application No. 21197168.4-1001, Extended European search report, dated Feb. 17, 2022.

* cited by examiner

MICROTOME BLADE GUARD WITH INTEGRATED BLADE ALIGNMENT DEVICE

FIELD

Microtomes or other tissue sample sectioning devices to produce sections of samples, and blade alignment devices for microtomes or other tissue sample sectioning devices.

BACKGROUND

Histology is a science or discipline associated with the processing of tissue for examination or analysis. The examination or analysis may be of the cellular morphology, chemical composition, tissue structure or composition, or other tissue characteristics.

In histology, a sample of tissue may be prepared for sectioning by a microtome or other sample sectioning device. Commonly, the tissue may be dried or dehydrated by removing most or almost all of the water from the tissue, for example by exposing the tissue to one or more dehydrating agents. After drying the tissue, clearing of the dehydrating agents may optionally be performed, and then an embedding agent (e.g., wax with added plasticizers) may be introduced or infiltrated into the dried tissue. The removal of the water and the infiltration of the embedding agent may aid in sectioning the tissue into thin sections with the microtome.

Embedding may then be performed on the tissue. During embedding, the tissue that has been dried and infiltrated with the embedding agent may be embedded in a block or other mass of wax, various polymers, or another embedding medium. Representatively, the dried and wax-infiltrated tissue may be placed in a mold and/or cassette, melted wax may be dispensed over the tissue until the mold has been filled with the wax, and then the wax may be cooled and hardened. Embedding the tissue in the block of wax may help to provide additional support during cutting or sectioning of the tissue with a microtome.

The microtome may be used to cut thin slices or sections of the sample of tissue. Various different types of microtomes are known in the arts. Representative types include, for example, sled, rotary, vibrating, saw, and laser microtomes. The microtomes may be manual or automated. Automated microtomes may include motorized systems or drive systems to drive or automate a cutting movement between the sample from which the sections are to be cut and a cutting mechanism used to cut the sections. It is to be appreciated that microtomes may also be used for other purposes besides just histology, and that microtomes may be used on other types of samples besides just embedded tissue.

BRIEF DESCRIPTION OF THE DRAWINGS

The invention may best be understood by referring to the following description and accompanying drawings that are used to illustrate embodiments of the invention. In the drawings.

DETAILED DESCRIPTION

In the following description, numerous specific details, such as particular microtomes, particular cutting drive systems, particular blade guards, and the like, are set forth. However, it is understood that invention may be practiced with various modifications to these specific details or, in some cases, without one or more of these specific details. In other instances, well-known components, circuits, structures and techniques have not been shown in detail in order not to obscure the understanding of this description.

The terminology used herein is for the purpose of describing particular examples only and is not intended to be limiting of the invention. Spatially relative terms, such as "beneath", "below", "lower", "above", "upper", and the like may be used herein for ease of description to describe one element's or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (e.g., rotated 90 degrees or at other orientations) and the spatially relative descriptors used herein interpreted accordingly.

As used herein, the singular forms "a", "an", and "the" are intended to include the plural forms as well, unless the context indicates otherwise. It will be further understood that the terms "comprises" and/or "comprising" specify the presence of stated features, steps, operations, elements, and/or components, but do not preclude the presence or addition of one or more other features, steps, operations, elements, components, and/or groups thereof.

The terms "or" and "and/or" as used herein are to be interpreted as inclusive or meaning any one or any combination. Therefore, "A, B or C" or "A, B and/or C" mean "any of the following: A; B; C; A and B; A and C; B and C; A, B and C." An exception to this definition will occur only when a combination of elements, functions, steps or acts are in some way inherently mutually exclusive.

Figure 1:
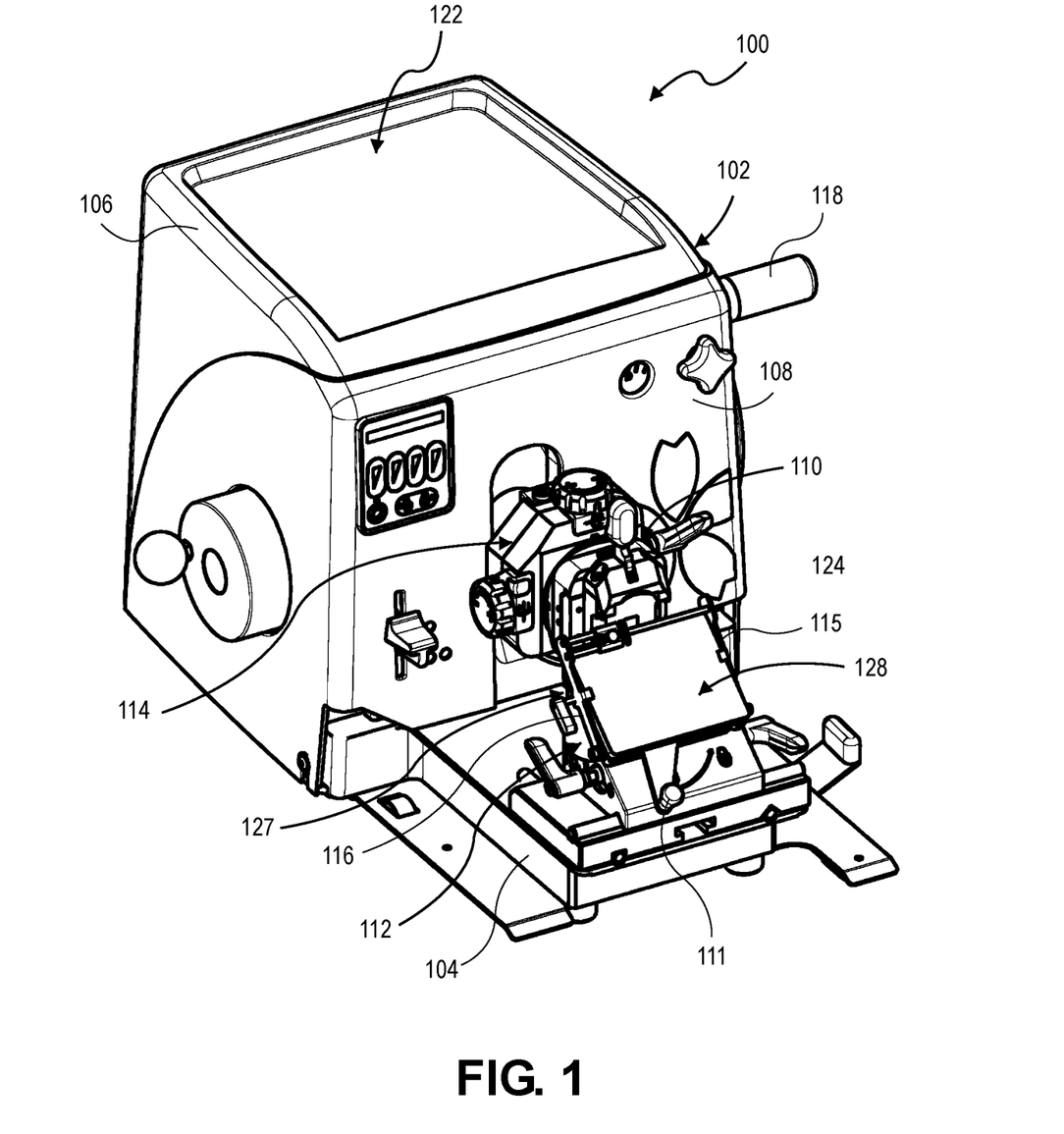
FIG. 1 illustrates a perspective top left side view of a sample sectioning device including a cutting member (blade or knife) in a slot in a blade block of the device.
Figure 2:
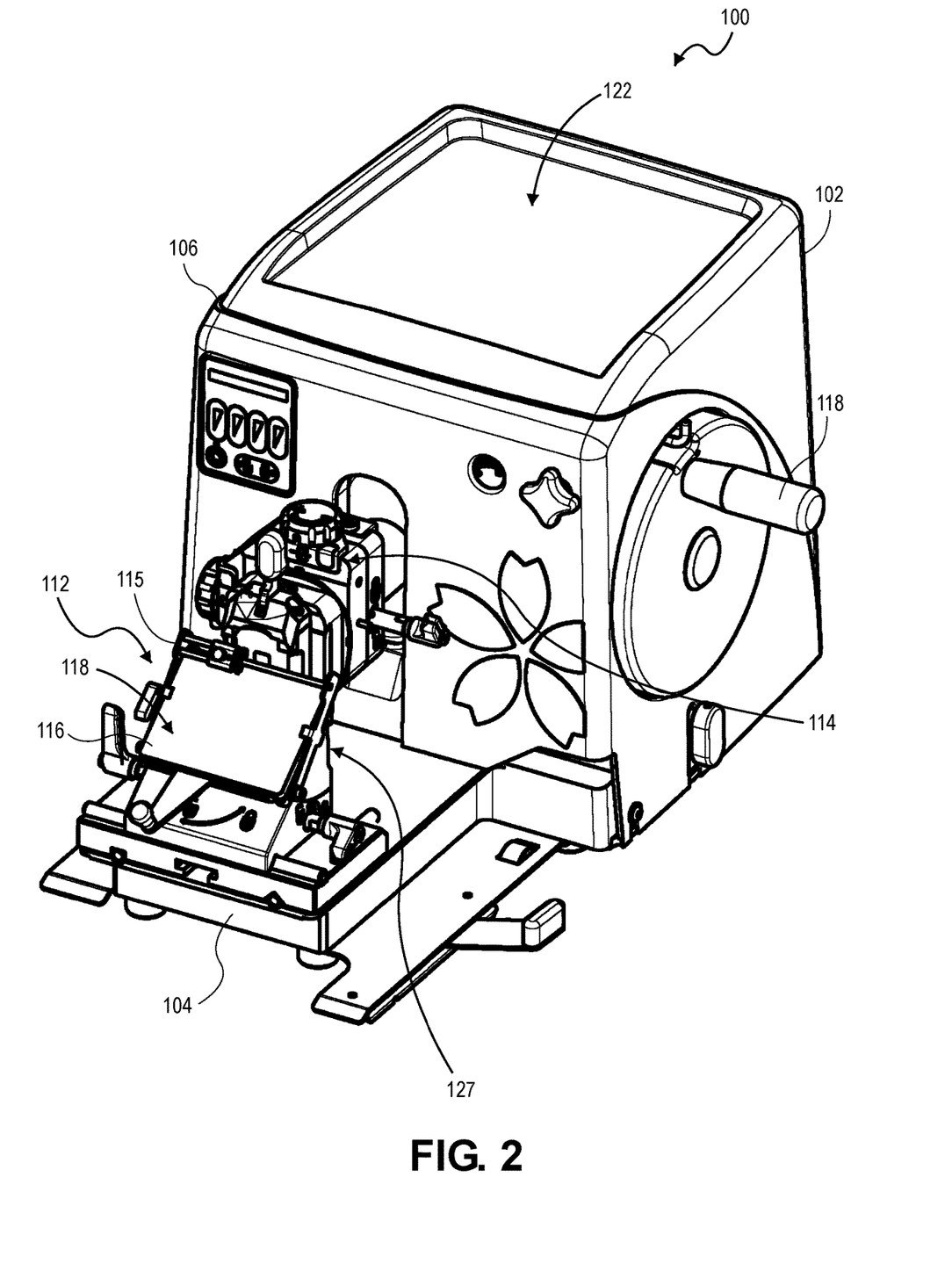
FIG. 2 illustrates a perspective top right side view of the sample sectioning device shown in FIG. 1.

FIG. 1 and FIG. 2 illustrate a microtome or other sample sectioning device. Microtome 100 may be a manual microtome, while in another embodiment, microtome 100 may be an automated microtome. Microtome 100 may include enclosure or housing 102 dimensioned to support and/or enclose various microtome components. For example, housing 102 may be a shell-like structure of a durable material such as plastic or metal (e.g., aluminum, carbon steel), which defines an interior enclosed space or chamber, within which microtome components can be positioned and enclosed, and an outer surface for supporting microtome components. The housing 102 may include base member 104, top portion 106 and front portion 108. Base member 104 is dimensioned to rest on a surface, such as a table, upon which the device is to be operated, and can support various sample sectioning instruments or components. Top portion 106 may be the upper most surface of the microtome housing 102, and in some cases, provide an area for storage of microtome accessories. Front portion 108 connects top portion 106 to base member 104.

Microtome 100 includes sectioning assembly 110 that may include various components, instruments, or the like for sample sectioning. Representatively, sectioning assembly 110 may include cutting mechanism 112 mounted to base member 104 and a sample holder 114 mounted to or disposed in an opening through front portion 108 of housing 102. Sample holder 114 may be dimensioned to receive and hold a sample (e.g., a paraffin embedded tissue sample) during a cutting operation. Sample could be a biological tissue that is taken from the body and embedded in paraffin wax. The tissue may include DNA, proteins, lipids, carbohydrates, fibers, connective tissue, or other types of tissue compounds or structures Cutting mechanism 112 may include blade block 116 that as shown in FIG. 1 and FIG. 2 has a body of two plates of similar length and width dimensions that are positioned on an angled base so that blade block 116 has a sloped front or receiving surface 128 (sloping away from rear surface 127 from the top toward the bottom as viewed). At a top or apex of the two plates of blade block 116 there is a slot between them for a cutting member to be removably placed therein. A suitable cutting member is, for example, knife or blade 124 suitable for cutting slices of a sample 126 held within the sample holder 114. Disposed between the two plates of blade block 116 and projecting forward of the blade block as viewed is lever 111. Rotation of lever 111 in one direction, e.g., clockwise, will cause a width of the slot to widen to allow for insertion or removal of blade 124 from the slot (an unlocked position of lever 111). Rotation of lever 111 in an opposite direction, e.g., counterclockwise, will cause a width of the slot to narrow to secure blade 124 therein (a locked position of lever 111).

Connected to a body of cutting mechanism 112 is blade guard 115. Blade guard 115 includes a first arm that is operable to be connected and in FIG. 1 and FIG. 2 is connected to a first side of cutting mechanism 112 of microtome 100 and a second arm operable to be connected and in FIG. 1 and FIG. 2 is connected to a second side of the cutting mechanism. In FIG. 1 and FIG. 2, the first arm and the second arm are connected to cutting mechanism 112 near a base of blade block 116. The first arm and second arm may be pivotally connected to blade block 112 by way of, for example, a screw, rivet or post that allows the arms to rotate. Blade guard 115 also includes a rod disposed between the first arm and the second arm. When blade guard 115 is connected to cutting mechanism 112, the rod may be positioned adjacent a blade slot of the cutting mechanism—forward of the blade slot so as not to interfere with a blade in the blade slot. The rod serves in one aspect as a guard or protective instrument to prevent the inadvertent contact of the blade by a user. Blade guard 115 also includes a staff connected to the rod and oriented to allow the staff to engage a blade positioned in the blade slot. Further details about a blade guard are presented below.

Sample holder 114 may move relative to cutting mechanism 112. For example, sample holder 114 may be connected to a feed drive system or cutting drive system that is operable to move sample holder in a vertical direction (e.g., up and down with respect to horizontal) while cutting mechanism 112 remains stationary. Alternatively, sample holder 114 (or portions of sample holder 114) may remain stationary while cutting mechanism 112 is moved, for example in a vertical direction (e.g., up and down) with respect to sample holder 114. Regardless of which component is moved, a vertical movement of sample holder 114 with respect to cutting mechanism 112 should be such that it causes the sample held within sample holder 114 to be sliced or sectioned. More specifically, a surface of a sample held by sample holder 114 may be sufficiently aligned parallel or a substantially parallel with cutting mechanism 112 and/or a cutting plane associated with cutting mechanism 112 and then sample holder 114 (or cutting mechanism 112) moved up and/or down to produce sufficiently evenly cut sample sections. It should be noted that terms such as "horizontal", "vertical", "top", "bottom", "upper", "lower", and the like, are used herein to facilitate the description of the illustrated device. It is possible for other devices to replace horizontal movements with vertical movements, etc. The sliced sample sections from sample 126 may be received by, for example, sloped receiving member 128 connected to blade block 116.

Microtome 100 may further include a storage member 122. Storage member 122 may include compartments or recessed regions that are designed to hold various microtome components. For example, storage member 122 may be configured to hold a tissue box, a slide, a carrier holding multiple slides or other instruments such as brushes or pencils a user may need while operating microtome 100. Storage member 122 may be integrally formed with the top portion 106 of microtome housing 102, may be a separate tray like structure that is removable attached to top portion 106, or a combination of an integrally formed member and a removable structure.

Referring again to FIG. 1 and FIG. 2, the movement of sample holder 114 may be controlled using hand wheel 118 (or a control device in the case of an automated microtome). Handle portion 118 may be associated with a wheel that may be rotated upon rotation of the handle. Rotation of hand wheel 118 may cause a vertical drive member associated with sample holder 114 (or cutting mechanism 112) to move in a vertical direction to facilitate slicing of a sample held by sample holder 114.

Figure 3:
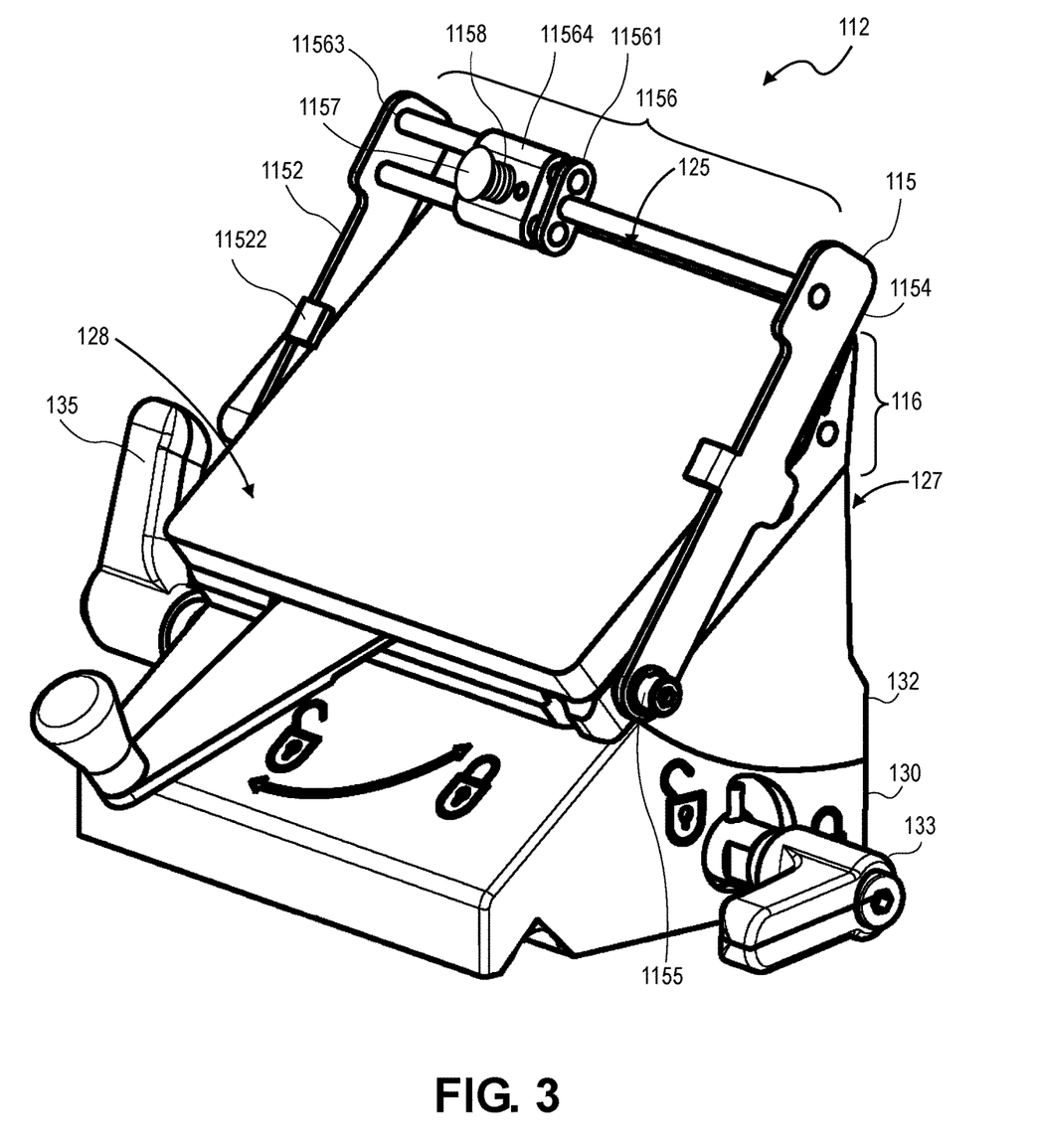
FIG. 3 illustrates a top perspective front side view of a cutting mechanism of the sample sectioning device of FIG. 1.
Figure 4:
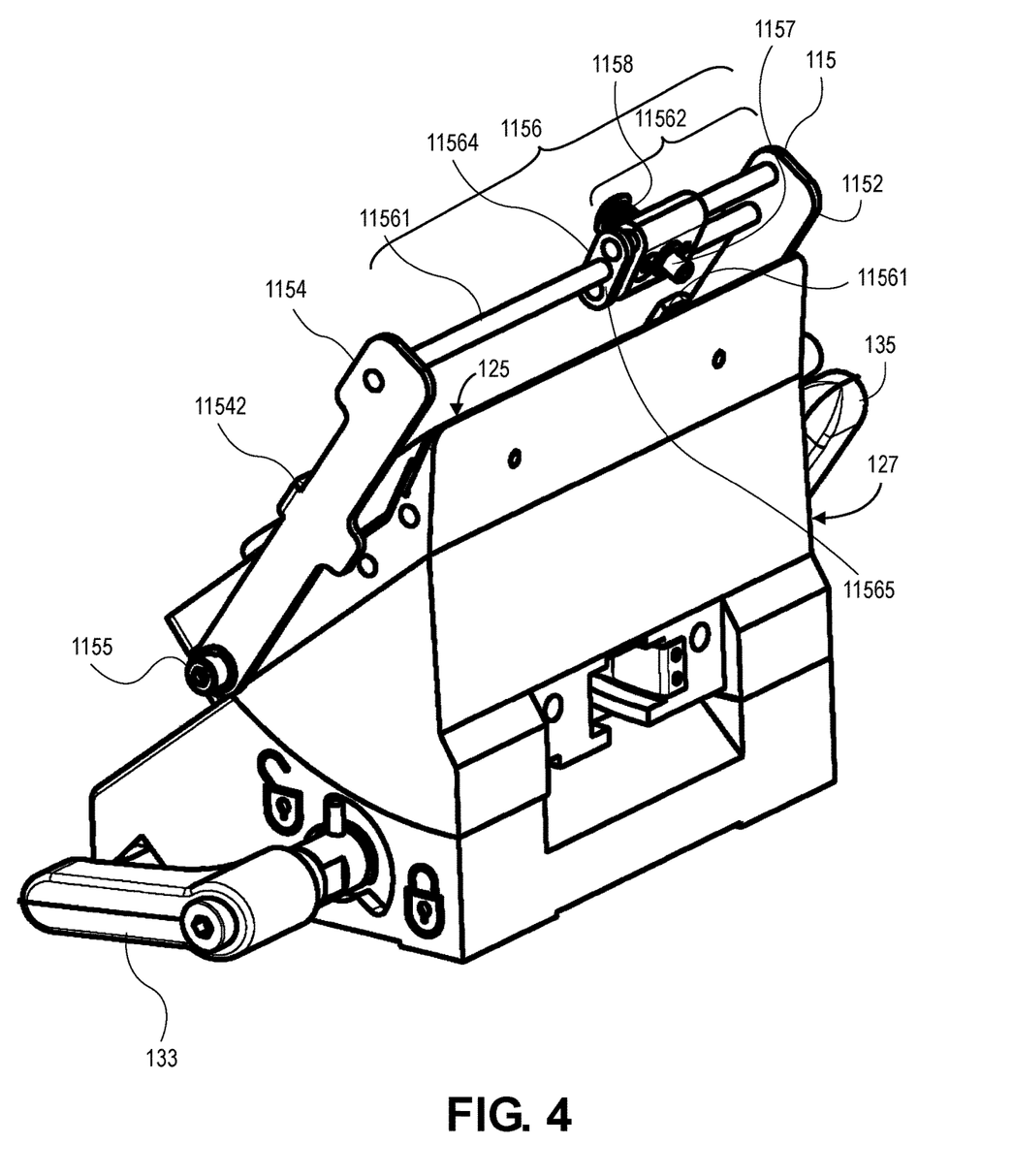
FIG. 4 illustrates a top perspective back side view of a cutting mechanism of the sample sectioning device of FIG. 1.

FIG. 3 and FIG. 4 show views of the cutting mechanism of microtome 100 isolated from the microtome. FIG. 3 is a front side perspective view and FIG. 4 is a rear side perspective view, with front and rear being from the perspective of a person operating the microtome. Cutting mechanism 112 includes knife holder base 130 having a body with a generally flat bottom or base that may be slidably connect to a front platform of microtome 100 (e.g., through a rail connection) to allow knife holder base 130 to be move toward or away front portion 108 of housing 102 of microtome 100 (see FIG. 1). A location of knife holder base 130 relative to front portion 108 may be fixed by locking knob 133. A side of knife holder base 130 opposite the bottom or base has an asymmetrical triangular shape when viewed from a side with a generally planar front side and concave back side. Disposed in slidable engagement with the concave back side of knife holder base 130 is arc support 132 that has a base with an arc shape opposed to the concave back side of knife holder base 130. Arc support 132 may be used to adjust an angle at which a cutting member (e.g., knife or blade) in cutting mechanism 112 cuts through a sample. A position of arc support 132 in knife holder base may be fixed by locking knob 135.

Referring to FIG. 3 and FIG. 4, connected to a top surface of arc support 132 is blade block 116. Blade block 116 has a body of two plates of similar length and width dimensions that are positioned on a front surface of arc support 132. A bottom plate of blade block 116 is generally rectangular with a triangular projection at its rear portion (triangular when viewed from the side). A top plate of blade block is also generally rectangular with an angled rear portion that conforms to the shape of projection on the bottom plate so that a top surface of the top plate is generally planar and defines a sloped front or receiving surface 128. The conforming angled portions of top plate and bottom plate define an apex of blade block 116 with a gap between the plates at the apex defining slot 125 for a cutting member such as a knife or blade to be removably placed therein. The bottom plate may have a front surface in slot 125 that includes a protruding step of a thickness for a base of a knife or blade to contact and to define a distance or depth into which a knife or blade my be inserted into slot 125.

Connected to a body of cutting mechanism 112 is blade guard 115. Blade guard 115 includes first arm 1152 connected to a first side of the bottom plate of blade block 116 and second arm 1154 connected to an opposite second side of the bottom plate of blade block 116. In FIG. 3 and FIG. 4, first arm 1152 and the second arm 1154 are connected to opposite sides of the bottom plate of blade block 116 near a front facing portion of the blade block (front relative to its position on microtome 100). The first arm and second arm may be pivotally connected to blade block 116 by way of a connector of, for example, a screw, rivet or post (e.g., connector 1155 connecting second arm 1154 to blade block 116) that allows the arms to rotate. First arm 1152 and second arm 1154 of blade guard 115 may be made of a durable material such as carbon steel or plastic. Rather than being connected to blade block 116, first arm 1152 and second arm 1154 may be connected to arc support 132 or to knife holder base 130.

Blade guard 115 also includes a lateral support member disposed between first arm 1152 and second arm 1154 at an end opposite the connectors (e.g., an end opposite connector 1155). FIG. 3 and FIG. 4 illustrate an example of a lateral support member in the form of rod 1156. Rod 1156 may be a single rod or rods or, as shown in FIG. 3 and FIG. 4, may include first rod portion 11561 and second rod portion 11562 that collectively span the distance between first arm 1152 and second arm 1154. First rod portion 11561 may be a single rod having a diameter on the order of, for example, 2.5 millimeters (mm) to 5.5 mm that is connected at one end to second arm 1154. Second rod portion 11562 may be two rods each of a diameter on the order of, for example, 2.5 mm to 5.5 mm that are each connected at one end to first arm 1152. The two rods of second rod portion 11562 may be parallel to one another and spaced from one another by gap 11563. First rod portion 11561 may be connected to second rod portion 11562 by fixed bracket 11565. As shown in FIGS. 3 and 4, bracket 11565 is connected to first rod portion 11561 by, for example, a weld or adhesive, and has openings having a diameter approximately equal to a diameter of each of the two rods of second rod portion 11562 so that the ends of each of the two rods are fixedly contained within bracket 11565. The two rods may also or alternatively be attached to bracket 1165 by a weld or adhesive. Disposed over/around second rod portion 11562 between bracket 1165 and first arm 1152 is sleeve or ferrule 11564. Sleeve 11564 may move along second rod portion 11562 between bracket 1165 and first arm 1152 (e.g., move left or right as viewed). In one example, a diameter of openings in sleeve 11564 for each of the two rods of second rod portion 1152 may be greater than the diameters of the rods themselves to allow the sleeve to traverse the rods. First rod portion 11561 and second rod portion 11562 may have similar lengths or, as shown in FIG. 3 and FIG. 4, first portion 11561 may have a longer length than second portion 11562 (e.g., first portion 11561 spans two-thirds of the distance between first arm 1152 and second arm 1154 and second portion 11562 spans one-third the distance). Rod 1156, including first rod portion and second rod portion, sleeve 11564 and bracket 11565 of blade guard 115 may be made of a durable material such as carbon steel or plastic.

When blade guard 115 is connected to blade block 116, rod 1156 may be placed in a closed position adjacent blade slot 125 of the blade block 116—forward of blade slot 125 so as not to interfere with a blade in the blade slot. First arm 1152 and second arm 1154 may each include a tab along their length that projects perpendicularly from a top surface of the respective arm a distance to contact surface 128 of blade block 116 to maintain a desired distance of rod 1156 from blade slot 125 when blade guard is in a closed position (see tab 11522 on arm 1152 and tab 11542 on arm 1154). Rod 1156 serves in one aspect as a guard or protective instrument to prevent the inadvertent contact of the blade by a user. Blade guard 115 may be rotated about connectors (e.g., connector 1155) forward to an open position to allow easier access to blade slot 125, such as for a blade change. First arm 1152, second arm 1154, rod 1156 and sleeve 11564 of blade guard 115 may be made of a durable material such as carbon steel or plastic.

Referring to FIG. 3 and FIG. 4, blade guard 115 also includes staff 1157 connected to rod 1156 and oriented to be operable to engage a blade in blade slot 125 of blade block 116 (e.g., oriented generally perpendicular to a length of the rod or rod portions). FIG. 3 and FIG. 4 show staff 1157 disposed through a body of sleeve 11564, such as between the two rods of second rod portion 11562. Staff 1157 is placed so that when blade guard 115 is in a closed position, staff may engage a blade positioned in blade slot 1125. Staff 1157 may have a length that is longer than a width of sleeve 11564. As shown in FIG. 3 and FIG. 4, spring 1158 is placed between a head of staff 1157 and sleeve 11564. Spring 1158 may serve to bias staff 1157 in a retracted position away from blade slot 1125 when blade guard 115 is in a closed position. Pressing on the head of staff 1157 with, for example, a finger may be sufficient to overcome the bias to advance staff forward toward blade slot 1125. Staff 1157 may have a head on one end and a second end that produces a magnetic field (e.g., a magnet). Where a material of the blade or knife is attracted to the magnetic field (e.g., a ferromagnetic material), staff 1157 may engage the blade or knife through contact or near contact and then move the blade or knife. In this manner, staff 1157 can adjust a position of a blade or knife in slot 125.

Figure 5:
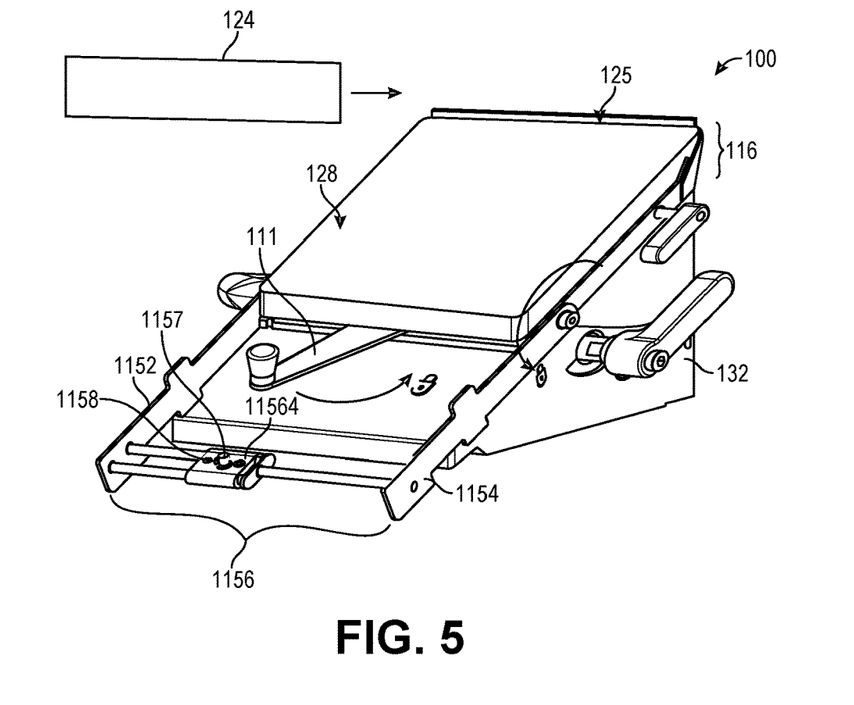
FIG. 5 illustrates a top perspective front side view of a portion of the cutting mechanism of the sample sectioning device of FIG. 1 with a blade guard rotated to an open position and shows an insertion of a blade or knife into a blade block of the cutting mechanism.
Figure 6:
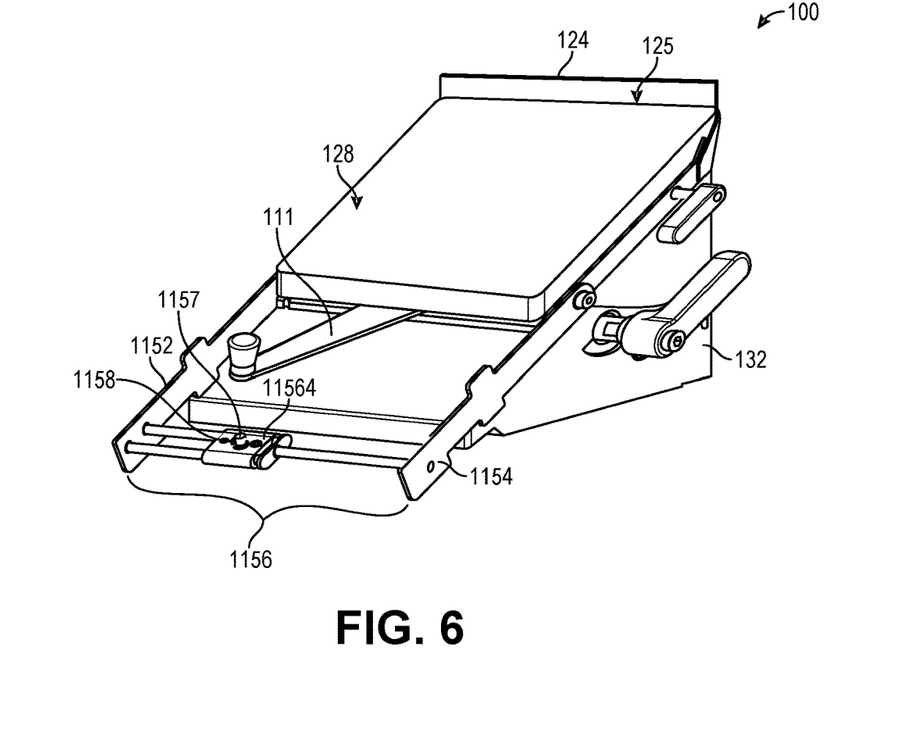
FIG. 6 illustrates a top perspective front side view of a portion of the cutting mechanism of the sample sectioning device of FIG. 1 with a blade guard rotated to an open position and shows a blade or knife after it is inserted into a blade block of the cutting mechanism.

FIGS. 5-8 show a method of loading and adjusting a blade or knife in microtome 100. FIG. 5 shows microtome 100 with blade guard 115 rotated, for example, by a technician, about connectors (e.g., connector 1155) forward (e.g., counterclockwise) to an open position to allow easier access by the technician to the blade slot. The technician may also rotate lever 111 to an unlocked position to widen a width of slot 125. With blade guard 115 out of the way and lever 111 in an unlocked position, the technician can insert blade or knife 124 into slot 125 in blade block 116. One way blade or knife 124 may be inserted is from a side of the blade block 116. Blade or knife 124 may be positioned so that a profile of the blade or knife aligns with a profile of slot 124 in blade block 116. Blade or knife 124 may then be introduced by the technician into slot 124 at one end (e.g., a left end) and slid or moved by the technician, for example, from a left side of blade block 116 toward a right side of the blade block until blade or knife 124 is completely in slot 125 (e.g., blade is at least flush with a left side blade block 116). FIG. 6 shows the assembly with blade or knife 124 completely in slot 125. While in slot 125, blade may not be oriented as desired by the technician that will be using the microtome to, for example, cut sections or thin slices of material (e.g., tissue sections).

Figure 7:
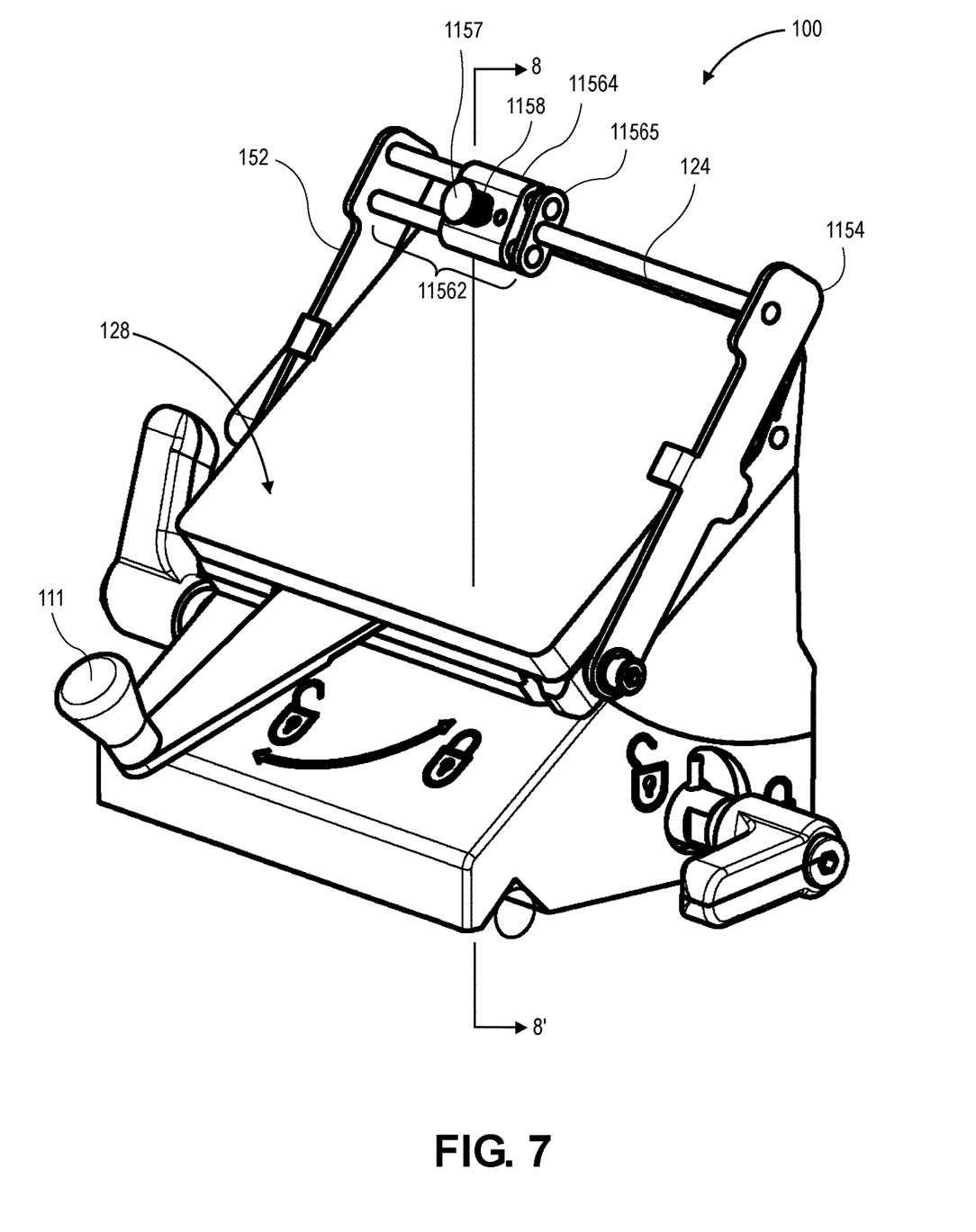
FIG. 7 illustrates a top perspective front side view of a portion of the cutting mechanism of the sample sectioning device of FIG. 1 with a blade or knife inserted into a blade block of the cutting mechanism and after a rotation of the blade guard to a closed position.
Figure 8:
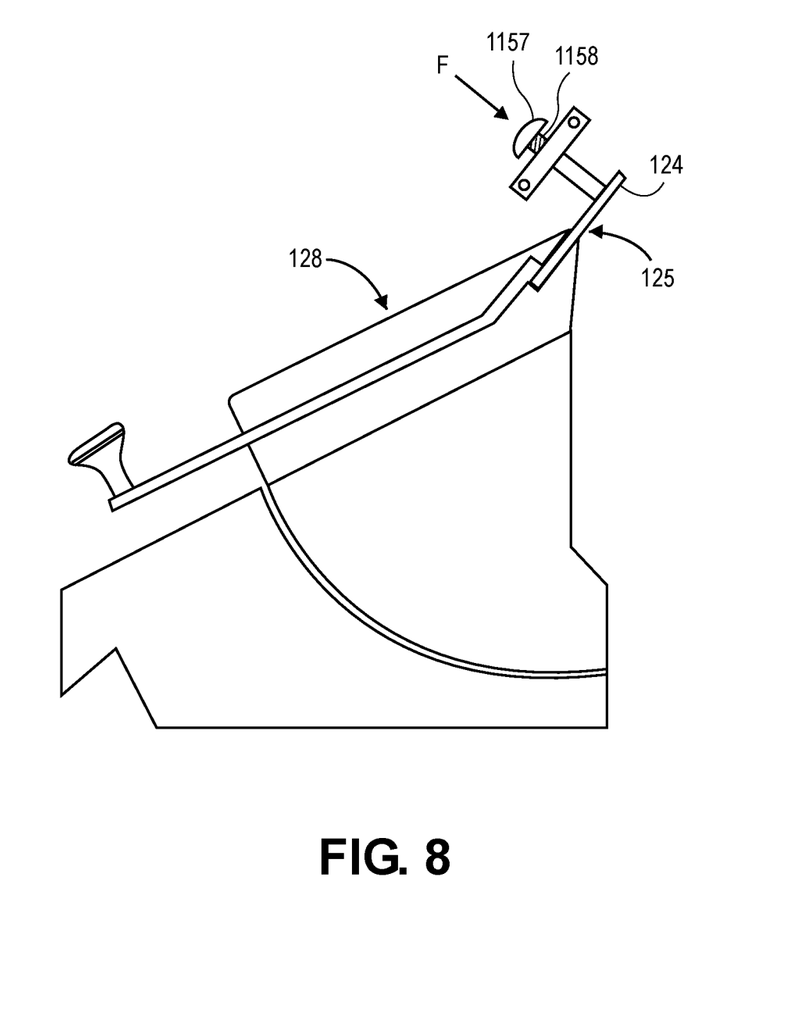
FIG. 8 shows a view of the cutting mechanism of FIG. 7 through line 8-8' and shows a staff of the blade guard engaging the blade or knife.

FIG. 7 shows microtome 100 with blade guard 115 rotated, for example, by a technician, about connectors (e.g., connector 1155) toward slot 125 (e.g., clockwise) to a closed position where the blade guard may serve a purpose of protecting the technician from contact with blade or knife 124. Once blade guard 115 is closed, staff 1157 connected to rod 1156 is in close proximity to blade or knife 124 in slot 125 but may be biased away from the blade by spring 1158 between a head of the staff and sleeve 11564. FIG. 8 shows the assembly of FIG. 7 through line 8-8' and shows a force, F, exerted on the head of staff 1157. The force, F, may be asserted by the technician and is sufficient to overcome the bias applied by spring 1158 and move staff 1157 toward blade or knife 124 in slot 125. An end of staff 1157 may engage blade or knife 124 through physical and/or magnetic attraction. Once blade or knife 124 is engaged by staff 1157, the technician may move staff 1157 laterally through the movement of sleeve 11564 on second rod portion 11562 to adjust a position of blade or knife 124 in slot 125. Once blade or knife 124 is in a desired position, the technician may rotate lever 111 to lock the blade or knife in position in slot 125. Cutting mechanism 111 of microtome 100 may now be in a position to cut sections or thin slices of material (e.g., tissue sections) with blade or knife 124.

Figure 9:
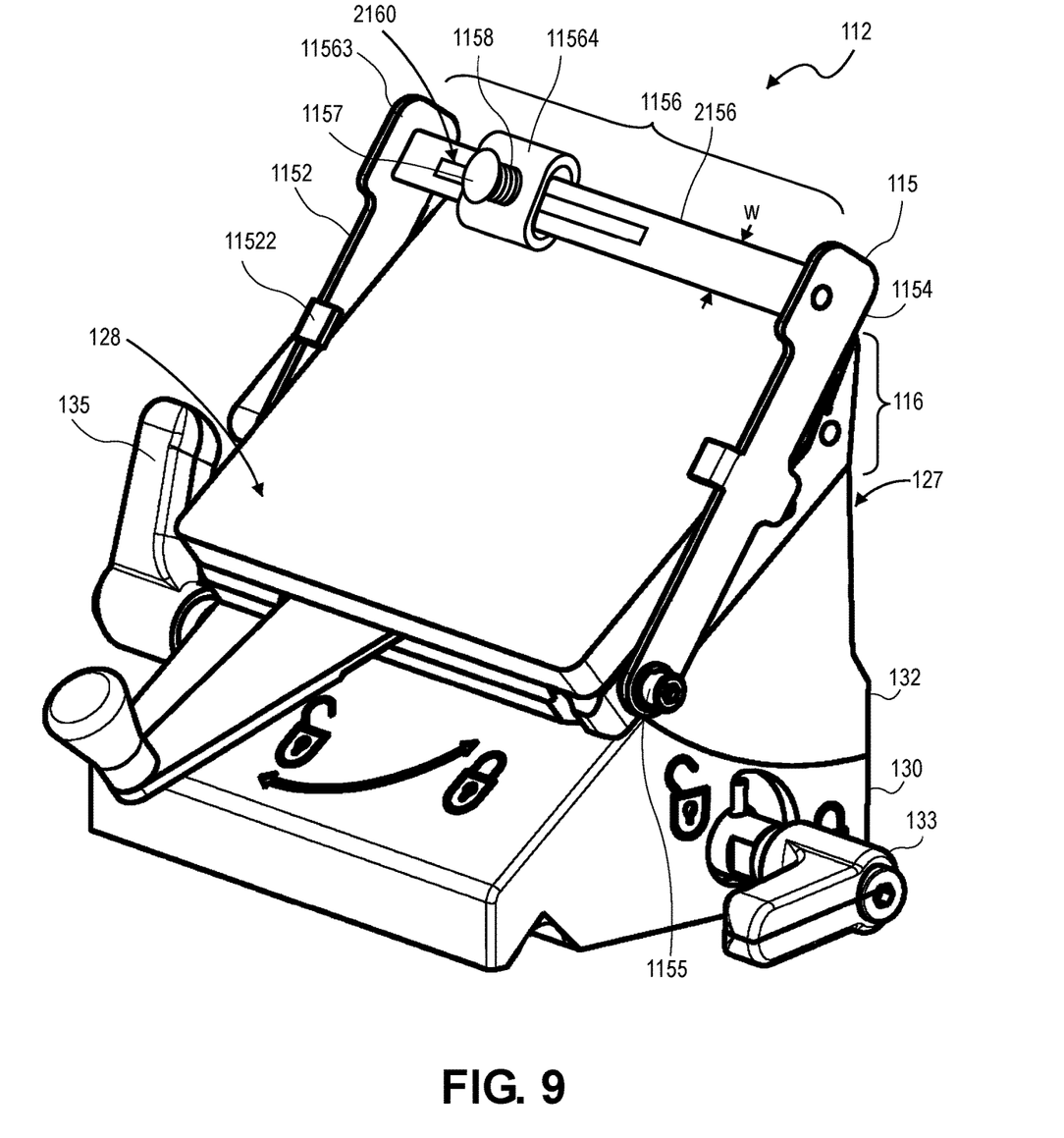
FIG. 9 shows a top perspective front side view of a cutting mechanism of a sample sectioning device having a blade guard that includes a lateral support member that is a plate or sheet.
Figure 10:
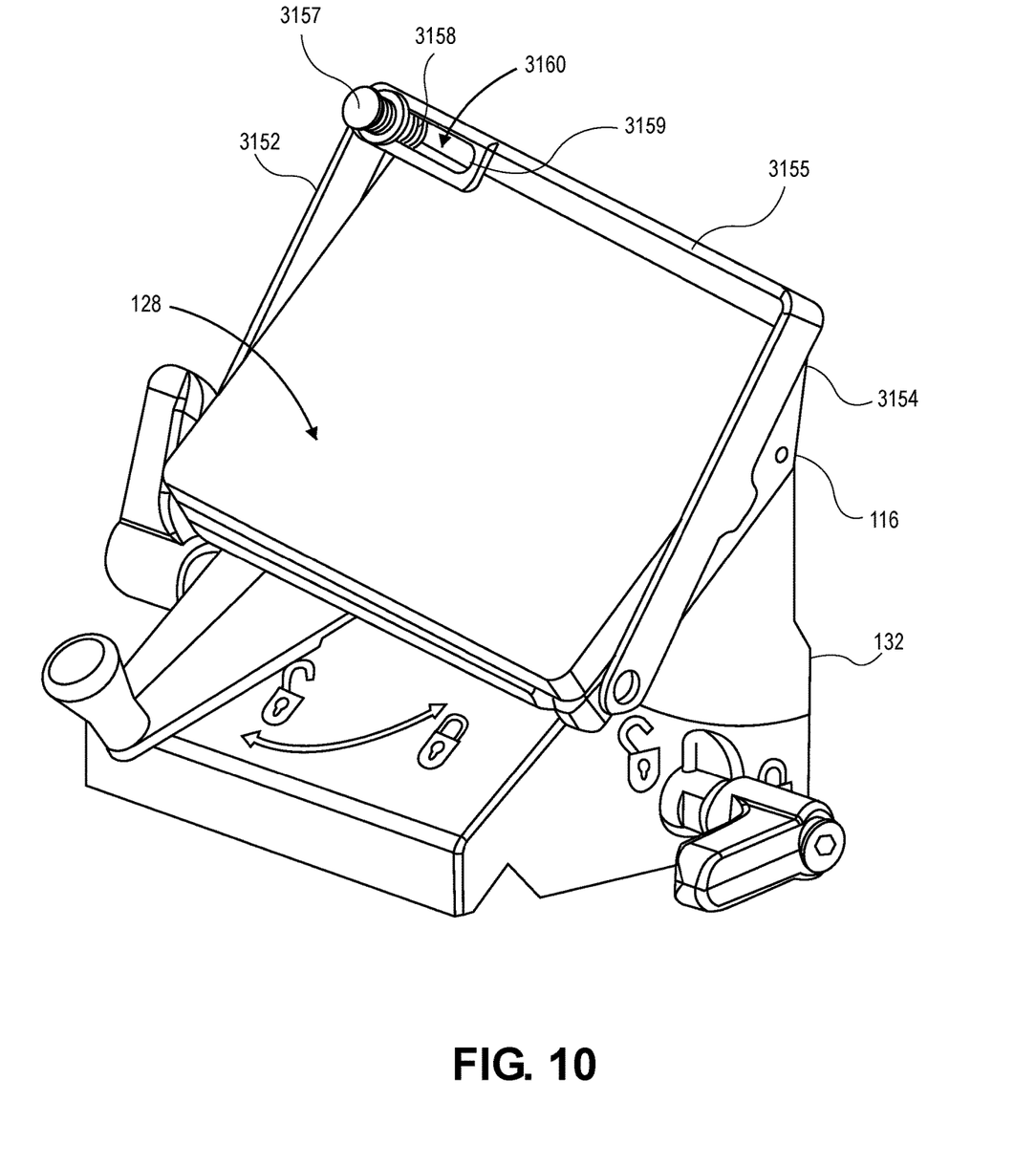
FIG. 10 shows a top perspective front side view of a cutting mechanism of a sample sectioning device having a blade guard that includes two arms connected by a cross member or transom with a lateral support member connected thereto.

In the illustrated example, a lateral support member between first arm 1152 and second arm 1154 of blade guard 115 was rod 1156 (first rod portion 11561 and second rod portion 11562). The lateral support member such as rod 1156 supports staff 1157 and allows staff 1157 to engage a blade or knife in slot 125 of blade block 116 and move the blade or knife (e.g., move the blade or knife laterally). Another example of a suitable lateral support is a plate or sheet, such as a rectangular plate or sheet of, for example, metal or plastic (e.g., clear plastic) that extends between first arm 1152 and second arm 1154. FIG. 9 shows a top perspective front side view of a cutting mechanism of a sample sectioning device similar to the cutting mechanism described above with respect to FIGS. 1-8, except that a blade guard of the device includes a lateral support member that is a plate or sheet. FIG. 9 shows plate or sheet 2156 connected at one end to first arm 1152 and at another end to second arm 1154. Plate or sheet 2156 has a width, w, on the order of, for example, 10 mm to 25 mm and may be an opaque material (e.g., carbon steel, aluminum, plastic) or a transparent or translucent material (e.g., clear plastic). Plate or sheet 2156 has laterally extending opening or slot 2160 into which staff 1157 may be inserted and secured. Staff 1157 may be biased by spring 1158 as in the previous example and may be moved (traversed) laterally within opening or slot 2160 by a technician to adjust a blade or knife in the sample sectioning device. A material of plate or sheet 2156 is durable or rigid enough to support staff 1157 and spring 1158. FIG. 10 shows a top perspective front side view of a cutting mechanism of a sample sectioning device where a blade guard includes two arms connected by a cross member or transom with a lateral support member connected thereto. In FIG. 10, the blade guard includes first arm 3152 and second arm 3154 each connected at one end to blade block 116. The blade guard also includes cross member 3155 connected to and disposed between first arm 3152 and second arm 3154. Cross member 3155, first arm 3152 and second arm 3154 may be formed as a single or unitary structure or joined by way of weld or adhesive to define an interconnected structure. The blade guard further includes lateral support member 3159 disposed between first arm 3152 and second arm 3154. FIG. 10 shows lateral support member 3155 disposed adjacent first arm 3152. Lateral support member 3155 may be connected to one or both of cross member 3155 and an arm (e.g., first arm 3152). Such connection may be fixed (e.g., by way of a weld or adhesive or clamp) or, where lateral support member 3155 is only connected to cross member 3155, may be slideable thereon. Lateral support member 3155 may be an opaque material (e.g., carbon steel, aluminum, plastic) or a transparent or translucent material (e.g., clear plastic) and has laterally extending opening or slot 3160 into which staff 3157 may be inserted and secured. Staff 3157 may be biased by spring 3158 as in the previous example and may be moved (traversed) laterally within opening or slot 3160 by a technician to adjust a blade or knife in the sample sectioning device.

Aspects

Aspect 1. A microtome blade guard comprising:
a first arm operable to be coupled to a first side of a cutting mechanism of a microtome;
a second arm operable to be coupled to a second side of a cutting mechanism;
a lateral support member disposed between the first arm and the second arm such that when the blade guard is coupled to a cutting mechanism, the lateral support member is operable to be positioned adjacent a blade slot of the cutting mechanism; and
a staff coupled to the lateral support member and operable to extend therefrom to engage a blade positioned in the blade slot.

Aspect 2. The microtome blade guard of Aspect 1, wherein the staff has a retracted position and an engagement position.

Aspect 3. The microtome blade guard of Aspect 1 or Aspect 2, wherein the staff is biased to the retracted position by a spring.

Aspect 4. The microtome blade guard of any of Aspects 1-3, wherein the staff comprises a portion that produces a magnetic field and wherein the engagement of the blade is through a magnetic attraction.

Aspect 5. The microtome blade guard of any of Aspects 1-4, wherein the staff is operable to move laterally along a length portion of the lateral support member.

Aspect 6. The microtome blade guard of any of Aspects 1-5, wherein the lateral support member comprises a rod or a plate.

Aspect 7. The microtome blade of Aspect 6, wherein the lateral support comprises a rod, the rod comprises a first rod coupled to the first arm and a second rod coupled to the first rod and to the second arm, wherein the staff is slidable along the second rod and wherein the lateral support comprises a plate, the plate comprises a laterally extending slot between the first arm and the second arm and the staff is operable to be moved in the laterally extending slot.

Aspect 8. The microtome blade guard of Aspect 7, wherein the second rod comprises two parallel and spaced rod portions and the staff is operable to project through a space defined by the two rod portions.

Aspect 9. The microtome blade guard of Aspect 7 or Aspect 8, wherein the first rod has a length that is longer than the second rod.

Aspect 10. A microtome comprising:
a blade block that having a blade slot that is operable to support a blade;
a sample holder that is operable to hold a sample to be sliced by the blade;
a drive system coupled to one of the blade block and the sample holder to drive a vertical movement of the one of the blade block and the sample holder relative to the other; and
a blade guard pivotally coupled to the blade block, the blade guard comprising a staff operable to engage a blade positioned in the blade slot.

Aspect 11. The microtome of Aspect 10, wherein the blade guard comprises:
a first arm operable to be coupled to a first side of the blade block;
a second arm operable to be coupled to a second side of the blade block; and
a lateral support member disposed between the first arm and the second arm, wherein the staff is coupled to the lateral support member.

Aspect 12. The microtome of Aspect 10 or Aspect 11, wherein the staff has a retracted position and an engagement position.

Aspect 13. The microtome of Aspect 12, wherein the staff is biased to the retracted position by a spring.

Aspect 14. The microtome of any of Aspects 10-13, wherein the staff comprises a portion that produces a magnetic field and wherein the engagement of the blade is through a magnetic attraction.

Aspect 15. The microtome of any of Aspects 10-14, wherein the staff is operable to move laterally along a length portion of the lateral support member.

Aspect 16. The microtome of any of Aspects 10-15, wherein the lateral support member comprises a rod or a plate.

Aspect 17. The microtome of Aspect 16, wherein the lateral support comprises a rod, the rod comprises a first rod coupled to the first arm and a second rod coupled to the first rod and to the second arm, wherein the staff is slidable along the second rod and wherein the lateral support comprises a plate, the plate comprises a laterally extending slot between the first arm and the second arm and the staff is operable to be moved in the laterally extending slot.

Aspect 18. The microtome of Aspect 17, wherein the second rod comprises two parallel and spaced rod portions and the staff projects through a space defined by the two rod portions.

Aspect 19. The microtome of Aspect 17, wherein the first rod has a length that is longer than the second rod.

Aspect 20. A method comprising:
placing a blade in a blade slot of a blade block of a microtome;
engaging the blade with a staff coupled to a blade guard that is coupled to the blade block; and
moving the blade with the staff.

Aspect 21. The method of Aspect 20, wherein engaging the blade with the staff comprises advancing the staff toward the blade.

Aspect 22. The method of Aspect 20 or Aspect 21, wherein the staff comprises a portion that produces a magnetic field and wherein the engaging the blade with the staff is through a magnetic attraction.

Whereas specific aspects of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of the invention which is to be given the full breadth of the claims and aspects appended and any and all equivalents thereof.

What is claimed is:
1. A microtome blade guard comprising:
a first arm operable to be coupled to a first side of a cutting mechanism of a microtome;
a second arm operable to be coupled to a second side of a cutting mechanism;
a lateral support member disposed between the first arm and the second arm such that when the blade guard is coupled to a cutting mechanism, the lateral support member is operable to be positioned adjacent a blade slot of the cutting mechanism; and
a staff comprising a head and an end, a distance between the head and the end defining a length coupled to the lateral support member between the first arm and the second arm and oriented with a length of the staff perpendicular to a length of the lateral support, the staff comprising a retracted position where the head of the staff is separated from the lateral support member by a first distance and being operable to be moved in a length direction from the retracted position to an engagement position where the head of the staff is separated from the lateral support member by a second distance that is less than the first distance by an application of a force to the head of the staff, wherein the staff is biased to the retracted position.

2. The microtome of claim 1, wherein the staff is biased to the retracted position by a spring.

3. The microtome blade guard of claim 1, wherein the staff comprises a portion that produces a magnetic field and wherein the engagement of the blade is through a magnetic attraction.

4. The microtome blade guard of claim 1, wherein the staff is operable to move laterally along a length portion of the lateral support member.

5. The microtome blade guard of claim 1, wherein the lateral support member comprises a rod.

6. The microtome blade of claim 5, wherein the rod comprises a first rod coupled to the first arm and a second rod coupled to the first rod and to the second arm, wherein the staff is slidable along the second rod.

7. The microtome blade guard of claim 6, wherein the second rod comprises two parallel and spaced rod portions and the staff is operable to project through a space defined by the two rod portions.

8. The microtome blade guard of claim 6, wherein the first rod has a length that is longer than the second rod.

9. A microtome comprising:
- a blade block comprising a first side and an opposite second side and defining a blade slot between the first side and the second side that is operable to support a blade;
- a sample holder that is operable to hold a sample to be sliced by the blade;
- a drive system coupled to one of the blade block and the sample holder to drive a vertical movement of the one of the blade block and the sample holder relative to the other; and
- a blade guard comprising a first arm pivotally coupled to the first side of the blade block and a second arm pivotally coupled to the second side of the blade block and a lateral support member disposed between the first arm and the second arm and positioned such that the first side of the blade block is between the lateral support member and the second side of the blade block, the blade guard comprising a staff comprising a head and an end, a distance between the head and the end defining a length, wherein the staff is coupled to the lateral support member between the first arm and the second arm, the staff comprising a retracted position where the head of the staff is separated from the lateral support member by a first distance and being operable to be moved from the retracted position toward the blade slot to an engagement position where the head of the staff is separated from the lateral support member by a second distance that is less than the first distance by an application of a force to the head of the staff to engage a blade positioned in the blade slot at a point between the first side of the blade block and the second side of the blade block, wherein the staff is biased to the retracted position.

10. The microtome of claim 9, wherein the staff is biased to the retracted position by a spring.

11. The microtome of claim 9, wherein the staff comprises a portion that produces a magnetic field and wherein the engagement of the blade is through a magnetic attraction.

12. The microtome of claim 9, wherein the staff is operable to move laterally along a length portion of the lateral support member.

13. The microtome of claim 9, wherein the lateral support member comprises a rod.

14. The microtome of claim 13, wherein the rod comprises a first rod coupled to the first arm and a second rod coupled to the first rod and to the second arm, wherein the staff is slidable along the second rod.

15. The microtome of claim 14, wherein the second rod comprises two parallel and spaced rod portions and the staff projects through a space defined by the two rod portions.

16. The microtome of claim 14, wherein the first rod has a length that is longer than the second rod.

* * * * *